United States Patent [19]
Weissman et al.

[11] Patent Number: 5,712,126
[45] Date of Patent: Jan. 27, 1998

[54] ANALYSIS OF GENE EXPRESSION BY DISPLAY OF 3-END RESTRICTION FRAGMENTS OF CDNA

[75] Inventors: Sherman M. Weissman; Yatindra Prashar, both of New Haven, Conn.

[73] Assignee: Yale University, New Haven, Conn.

[21] Appl. No.: 510,032

[22] Filed: Aug. 1, 1995

[51] Int. Cl.$^6$ .............................. C12P 19/34; C12Q 1/68
[52] U.S. Cl. .......................... 435/91.2; 435/6; 435/91.1; 435/91.5; 435/91.51; 435/91.52
[58] Field of Search .............................. 435/6, 91.2, 91.1, 435/91.5, 91.51, 91.52; 536/24.2, 24.33, 24.3

[56] References Cited

U.S. PATENT DOCUMENTS 5,459,037  10/1995  Sutcliffe et al. .............................. 435/6

FOREIGN PATENT DOCUMENTS 0534858  3/1993  European Pat. Off. .

OTHER PUBLICATIONS

Fischer et al., "Restriction fragment length polymorphism–coupled domain-directed differential display: A highly efficient technique for expression analysis of multigene families," *Proc. Natl. Acad. Sci. USA* 92:5331–5335, 1995.

Frohman et al., "Rapid production of full-length cDNAs from rare transcripts: Amplification using a single gene-specific oligonucleotide primer," *Proc. Natl. Acad. Sci. USA* 85:8998–9002, 1988.

Ko et al., "Unbiased amplification of a highly complex mixture of DNA fragments by 'lone linker' –tagged PCR, "*Nucleic Acids Research* 18(14):4293–4294, 1990.

Liang and Pardee, "Differential Display of Eukaryotic Messenger RNA by Means of the Polymerase Chain Reaction," *Science* 257: 967–971, 1992.

Loh et al., "Polymerase Chain Reaction with Single-Sided Specificity: Analysis of T Cell Receptor δ Chain," *Science* 243:217–220, 1989.

Prashar and Weissman, "Analysis of differential gene expression by display of 3' end restriction fragments of cDNAs," *Proc. Natl. Acad. Sci. USA* 93:659–663, 1996.

Roux and Dhanarajan, "A Strategy for Single Site PCR Amplification of dsDNA: Priming Digested Cloned or Genomic DNA from an Anchor–Modified Restriction Site and a Short Internal Sequence," *BioTechniques* 8(1):48, 1990.

Averboukh et al., "Better Gel Resolution and Longer cDNAs Increase the Precision of Differential Display," *BioTechniques* 20(5):918–921, 1996.

Zhao et al., "New Primer Strategy Improves Precision of Differential Display," *BioTechniques* 18(5):842–850, 1995.

Liang et al., "Differential Display and Cloning of Messenger RNAs from Human Breast Cancer versus Mammary Epithelial Cells," *Cancer Research* 52:6966–6968, 1992.

Liang et al., "Distribution and cloning of eukaryotic mRNAs by means of differential display: refinements and optimization," *Nucleic Acids Research* 21(14):3269–3275, 1993.

Reeves et al., "General Method for PCR Amplification and Direct Sequencing of mRNA Differential Display Products," *Biothechniques* 18(1):18–20, 1995.

Liang et al. (1994) Nucleic Acids Research 22:5763–4.

Zeng et al. (1994) Nucleic Acids Research 22:4381–5.

Cecchini et al. (1993) Nucleic Acids Research 21:5742–7.

Duguid and Dinauer (1990) Nucleic Acids Research 9:2789–92.

Liang et al. (1993) Nucleic aCids Research 21:3269–75.

Wang and Brown (1991) Proc. Natl. Acad. Sci. USA 88:11505–9.

(List continued on next page.)

*Primary Examiner*—W. Gary Jones
*Assistant Examiner*—Amy Atzel
*Attorney, Agent, or Firm*—Seed and Berry LLP

[57] ABSTRACT

The present invention provides methods to analyze gene expression by selective PCR amplification and display of 3'-end restriction fragments of double stranded cDNAs.

16 Claims, 4 Drawing Sheets

OTHER PUBLICATIONS

Lisistyn et al. (1993) Science 259:946–51.
Navarro et al. (1996) J. Virol. Methods 56:59–66.
Diachenko et al. (1996) Biochemical and Biophysical Research Communications 219:824–8.
Kato (1995) Nucleic Acids Research 23:3685–90.
Kato (1996) Nucleic Acids Research 24:394–5.
Chenchik et al. (1996) BioTechniques 21:526–34.
Vectors from nucleic acid databases.

ANALYSIS OF GENE EXPRESSION BY DISPLAY OF 3-END RESTRICTION FRAGMENTS OF CDNA

STATEMENT OF GOVERNMENT INTEREST

This invention was made, at least in part, with government support under grant number CA-42556-10, awarded by the Department of Health and Human Services. As such, the government may have certain rights in the invention.

BACKGROUND OF THE INVENTION

The identification of genes associated with development, differentiation, disease states, and response to cellular environment is an important step for advanced understanding of these phenomena. Specifically, effective methods for conducting genetic analysis are needed to identify and isolate those genes that are differentially expressed in various cells or under altered cell environments.

Early methods developed to identify and clone such genes were primarily based on the principle of differential or subtractive hybridization [see Proc. Natl. Acad. Sci. USA 88:2825 (1991); Nature 308:149 (1984); Proc. Natl. Acad. Sci. 84:1609 (1987); and Mol. Cell Biol. 9:1041 (1989)]. Despite the usefulness of these methods, they can only analyze a fraction of the overall changes in gene expression, require large amounts of ribonucleic acid (RNA), and are lengthy and labor intensive.

Recently, Liang and Pardee [see Science 257:967 (1992)] developed a gel-based technique that facilitates a rapid and extensive analysis of differentially-expressed messenger RNA (mRNAs). Very briefly, this technique was directed toward the identification of differentially expressed genes among the approximately 15,000 individual mRNA species in a pair of mammalian cell populations, and then recovering their complementary deoxyribonucleic acid (cDNA) and genomic clones. The general strategy was to amplify partial complementary cDNA sequences from subsets of mRNAs by reverse transcription and the polymerase chain reaction. These short sequences would then be displayed on a sequencing gel. In this technique, pairs of 10-mer primers were selected so that each would amplify CDNA from about 50 to 100 mRNAs, because this number was optional for display on the gel [Science 257:967 (1992); and see also U.S. Pat. No. 5,262,311, the disclosure of which is incorporated in toto herein].

Several groups have successfully employed the Liang and Pardee technique to identify differentially expressed genes [see Trends Genet. 11:242 (1995); Curr. Opinion Immunol. 7:274 (1994); and Nucleic Acids Res. 19:4009 (1994)]. However, certain limitations associated with this technique—limitations such as the lack of quantitative correlation with mRNA abundances, a significant incidence (up to 80%) of false positive signals, variable reproducibility of the display patterns, multiple sequences migrating in the gel to produce a single signal, and under-representation and redundancy of mRNA signals [see Trends Genet. 11:242 (1995); Nucleic Acids Res. 22:5763 (1994); and FEBS Let. 351:231 (1994)]—have made it difficult to fully evaluate differential gene expression. More importantly, the size of bands is not always readily predictable from the mRNA sequence.

Amplification of cDNAs at the low primer annealing temperature of 40° to 42° C., a non-stringent PCR condition, as in the Liang and Pardee technique is now considered to be a major limitation of current gel display protocols [see Trends Genet. 11:242 (1995); Biotechniques 18:842 (1995); and Biochem. Biophy. Res. Commun. 199:564 (1994)]. Adaptations of the original protocol have been reported in order to overcome some of these limitations, such as the use of one base anchored oligo dT primer for increased representation of mRNAs [see Nucl. Acid. Res. 22:5763 (1994)], and the use of long composite primers to achieve reproducible patterns under more stringent PCR conditions [see Nucl. Acid. Res. 22:5763 (1994); and FEBS Let. 351:231 (1994)]. However, all these modifications continue to involve annealing of arbitrary primers at approximately 40° to 42° C. for the first ten rounds of amplification.

SUMMARY OF THE INVENTION

According to the present invention, an alternative approach is provided for cDNA display on gels to those described by Liang and Pardee or those described in subtractive or differential hybridization techniques. Display patterns are generated when restriction enzyme digested double stranded (ds) cDNA is ligated to an adapter that mediates selective PCR amplification of 3'-end fragments of cDNAs under high stringency PCR conditions, instead of non-stringent arbitrary cDNA amplification as taught by Liang and Pardee.

In the present invention, a diversity of patterns is generated by choosing different sets of restriction enzymes and anchored oligo-dT primers. Since all cDNAs in a sample acquire a common heel (a "heel" is a DNA sequence not presented in the DNA being synthesized) from the oligo-dT primer during synthesis, most cDNA molecules in a subset (determined by the anchor nucleotides of the oligo-dT) can be displayed by choosing a combination of restriction enzymes while minimizing under-representation or redundant-representation of mRNAs. This approach provides near-quantitative information about the levels of gene expression, can resolve hidden differences in the display gel, produces a single band for each mRNA species, and produces bands of predictable size for known gene sequences. Most importantly the method according to the present invention produces consistently reproducible display patterns.

Accordingly, the aspect of the present invention is to describe an assay method that, when compared to presently used methods for such assays, achieves a decrease in false positive signals; provides a reproducible technique for identifying and displaying gel patterns of DNA; provides a means for distinguishing multiple sequence signals for sequences that co-migrate to a single band in conventional techniques; avoids under representation and redundancy of RNA; and utilizes stringent conditions for PCR annealing.

This and other aspects of the present invention will become clearly understood by reference to the following figures, examples, and description of the invention.

DETAILED DESCRIPTION OF THE INVENTION

Interestingly enough, during the making of the present invention, RNA expression during early T-cell activation, an extensively studied phenomenon associated with the induction of a large number of genes within a relatively short period of time [see Annu. Rev. Immunol. 8:421 (1990); and Curr. Opinion Immunol. 7:327 (1995)], was studied as the test system. Curiously, there is a limited description of genes that are down-regulated upon T-cell activation [see Nucleic Acids Res. 19:4655 (1991); and Proc. Natl. Acad. Sci. USA 90:10260 (1993)] and the present approach offered a convenient method for looking for such products.

Figure 1:
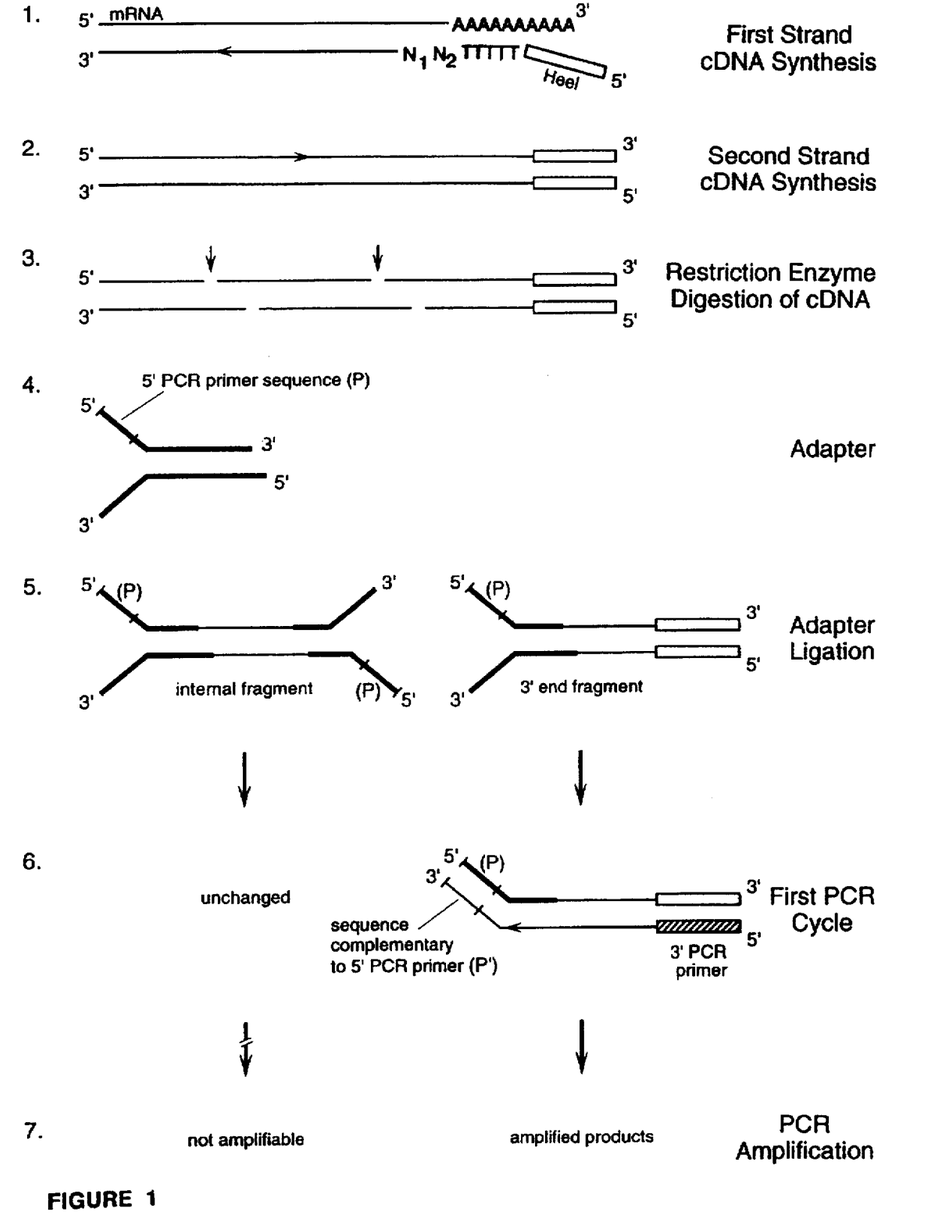
FIG. 1 is an outline schematic of the method for 3'-end cDNA amplification according to the present invention.

The general 7-step scheme for the method according to the present invention is shown in FIG. 1. A two base anchored, oligo-dT primer with a 3' heel is used for first strand synthesis by Gubler-Hoffman method [see Gene 25:263 (1983)] All cDNA molecules thus acquire a common 3' heel. This cDNA is digested with a restriction enzyme and ligated to a Y-shaped adapter similar in principle to the bubble adapter [see Nucleic Acids Res. 18:2887 (1990)]. The "Y" adapter is synthesized with an overhang on its 3'-end for ligation, and on its 5'-end it has a stretch of non-complementary sequence on the opposite strands that provides for its 'Y' shape. The 5' PCR primer is synthesized from this Y region and cannot anneal to the adapter itself. The upstream fragments of digested cDNA with adapter ligated on both the ends, or only one end in the 5' terminal piece will, therefore, not be PCR amplified. However, the 3' primer anneals to the heel of the 3'-end fragments of cDNA during the first PCR cycle and extends DNA synthesis into the Y region of the ligated adapter, thus synthesizing complementary sequences to which the 5' PCR primer can now anneal. The two PCR primers can then selectively amplify the 3'-end fragments of the cDNA under stringent PCR conditions.

More specifically FIG. 1 presents a method whereby a two base anchored oligo-dT primer with an added heel is used for first strand cDNA synthesis from total RNA using reverse transcriptase (step 1). This is followed by a second strand synthesis using the Gubler-Hoffman method (step 2). All cDNA molecules synthesized according to these two steps will thus acquire a common 3' heel. Next the cDNA is digested (step 3) with a selected restriction enzyme (at this point restriction enzymes that produce either blunt ends or overlapping ends may be used, however, in the following examples the enzyme BstY1 is depicted which produced overhanging ends) and ligated to a previously synthesized Y-shaped adapter (step 4). The adapter has an overhang on its 3'-end for ligation, and on its 5'-end has a stretch of non-complementary sequences that provide for its shape. The 5' PCR primer is made from this Y region (step 4) and thus cannot anneal to the adapter itself. The upstream fragments of digested cDNA with adapter ligated on both the ends (step 5) or only one end in the 5' terminal piece will, therefore, not be PCR amplified. However, the 3' primer will anneal to the heel of the 3'-end fragments of cDNA (step 5) during the first PCR cycle and extend DNA synthesis into the Y region of the ligated adapter, thereby synthesizing synthesizing complementary sequences to which the 5' PCR primer can now anneal (step 6). The two PCR primers can then selectively amplify the 3'-end fragments of the cDNA under stringent conditions (step 7).

Each six base cutter restriction enzyme cuts approximately 8% of the cDNAs at positions between 50 and 400 bases from the polyA tract, so that more than 12 six base cutters will be needed to approach complete representation of cDNAs, each being used with several different anchored oligo-dT primers. Also, we estimate that at best about 100-150 discrete bands can be detected in a single gel lane. Therefore, at least 100 lanes will need to be run under different conditions to study the overall pattern of gene expression in any single cell type.

A major advantage of the present approach is that the size of a known cDNA product and hence its position on the display gel is predictable. Interleukin-2 (IL-2) is a well studied cytokine expressed only in activated and not resting T-cells [see Annul. Rev. Immunol. 8:421 (1990)] and should be displayed as band of predictable size. To confirm this and to test the ability of the method to display differences, cDNA from resting and activated human peripheral blood T-lymphocyte RNA were made using oligo-dT primer with a heel and 3' anchor residues TA complementary to the AT dinucleotide in the IL-2 mRNA sequence immediately preceding the polyA tail. Restriction digestion with BstY1 should produce, and did when tested, a 146 bp 3'-end fragment of IL-2 cDNA [see Natl. Acad. Sci. USA 81:2541 (1984)]. When added to the sizes of the 3' oligo dT and 5' adapter, this should, and did, produce a band of 209 bp on the display gel. A distinct band of the predicted size was produced in activated (FIG. 2, lane 2) (FIG. 2, lane 1) but not in the resting T-cell sample on display of BstY1 cut cDNA DNA sequence analysis of this fragment confirmed the presence of the 5' adapter followed by a BstY1 site, IL-2 3'-end sequences, the polyadenylation signal AATAAAA (SEQ. NO. 1), the downstream oligo-A tract and the heel primer.

EXAMPLE 1

Conditions for growth and activation of Jurkat and peripheral blood T-cells, respectively, have been previously described [see Proc. Natl. Acad. Sci. USA 90:10260 (1993); and J. Exp. Med. 174:1259 (1991), the disclosures of which are incorporated herein in toto]. Total cellular RNA was prepared from untreated (J0) and 4 hour Phorbol 12-Myristate 13-Acetate (PMA) plus Phytohemagglutinin (PHA) activated Jurkat cells (JTP) using RNAzol (Bibco-BRL). Synthesis of cDNA was performed according to the manufacturer's instructions (Gibco-BRL kit for cDNA synthesis). The reaction mixture for first strand synthesis included, 10 µg total RNA, 2 pmols of one of the following three nucleotide anchored heeled oligo-dT primers (wherein T18 refers to a string of 18 thymine-based nucleotides):
RP5.0 CTCTCAAGGA TCTTACCGCT.T$_{18}$AT 40 (SEQ. NO. 2);
RP6.0 TAATACCGCG CCACATAGCA T$_{18}$CG 40 (SEQ. NO. 3); or
RP9.2 CAGGGTAGAC GACGCTACGC T$_{18}$GA 40 (SEQ. NO. 4)
along with other conventional reagents for the first strand synthesis reaction except reverse transcriptase. In these three sequences, the "true" heel is to be considered to be the first 20 nucleotides (that is the molecule without the T$_{18}$AT, T$_{18}$CG, or T18$_{GA}$ portion. Thus, the "true" heels are
CTCTCAAGGA TCTTACCGCT 20 (SEQ. NO. 10);
TAATACCGCG CCACATAGCA 20 (SEQ. NO. 11); and
CAGGGTAGAC GACGCTACGC 20 (SEQ. NO. 12).

The reaction mixture was layered with mineral oil, incubated at 65° C. for 7 minutes followed by 50° C. for another 7 minutes. At this stage 2 µl of Superscript reverse trascriptase (200 u/µl, Gibco-BRL) was added quickly, mixed, and the reaction continued for an additional hour at 50° C. Second strand synthesis was performed at 16° C. for 2 hours. At the end of the reaction the cDNAs were precipitated with ethanol and the yield (approximately 100 ng) of cDNA was calculated.

The adapter of the following A1 and A2 nucleotide molecules was next synthesized with the following sequences:

A1 TAGCGTCCGG CGCAGCGACG GCCAG 25 (SEQ. NO. 5); and

A2 GATCCTGGCC GTCGGCTGTC TGTCGGCGC 29 (SEQ. NO. 6)

One μg of oligonucleotide A1 was first kinased at the 5'-end in a final reaction volume of 10 μl using T4 polynucleotide kinase (PNK) with conventional techniques. After phosphorylation, PNK was heat denatured, and 1 μg of the oligo A2 was added along with 10× annealing buffer (1M NaCl, 100 mM Tris, HCl pH 8.0, and 10 mM EDTA pH 8.0) in a final working volume of 20 μl. This mixture was then heated at 65° C. for 10 minutes, followed by slow cooling to room temperature for 30 minutes. This results in the formation of the "Y" adapter at a final concentration of 100 ng/μl. About 20 ng of the cDNA was digested with 4 units of BgI II in a 10 μl reaction for 30 minutes. Two μl (~4 ng digested cDNA) of this reaction mix was then used for ligation to 100 ng (~50 fold) of the Y-shaped adapter. The ligation was carried out for 16 hrs at 15° C. in a final volume of 5 μl (2 μl digested cDNA, 1 μl adapter, and 2 μl of a solution containing 5 μl 10 mM ATP, 5 μl 10× ligation buffer, and 10 μl (4 units) of T4 DNA ligase. Following ligation, the reaction mixture was diluted to a final volume of 80 μl (adapter ligated cDNA conc. ~50 pg/μl) and heated at 65° C. for 10 minutes to denature T4 DNA ligase, and 2 μl aliquots (with ~100 pg cDNA) were used for PCR.

The following sets of primers were used for PCR amplification of the adapter ligated 3'-end cDNAs. The RP5.0, RP6.0 or RP9.2 primers were used as the 3' primer, while the following:

A1.1 TAGCGTCCGG CGCAGCGAC 19 (SEQ. NO. 7) served as the 5' primer. In order to detect the PCR products on the display gel, oligo A1.1 was 5'-end labeled for 30 minutes in a final reaction volume of 20 μl containing 24 pmoles of this oligo, 10 units of PNK, and 48 pmoles, i.e., 15 μl of γ32P ATP (Amersham). PNK was heat denatured at 65° C. for 20 minutes and the labelled oligo was mixed with 60 μl of 2 μM of unlabelled oligo 1.1 (at a 1:4 dilution, final oligo concentration of ~2 μM). The PCR reaction mixture (20 μl) consisted of 2 -1 (~100 pg) of the template, 2 μl of 10× PCR buffer (100 mM Tris.HCl and 500 mM KCl), 2 μl of 15 mM MgCl$_2$ to yield 1.5 mM final Mg$^{+2}$ concentration that is optimum for the reaction, 200 μM of dNTPs, 200 nM each of 5' and 3' PCR primers, and 1 unit of Amplitaq. Primers and dNTPs were added after preheating the reaction mixture containing the remainder of the components at 85° C. This "hot start" PCR was done to avoid artefactual amplification arising out of arbitrary annealing of PCR primers at lower temperature during transition from room temperature to 94° C. in the first PCR cycle. PCR consisted of 28 to 30 cycles at the stringent conditions of 94° C. for 30 seconds, 56° C. for 2 minutes, and 72° C. for 30 seconds. A higher number of cycles resulted in smeared gel patterns.

PCR products (2.5 μl) were analyzed on a 6% polyacrylamide sequencing gel. For double or multiple digestion following adapter ligation, 13.2 μl of the ligated cDNA sample was digested with secondary restriction enzymes in a final volume of 20 μl. From this solution, 3 μl was used as the template for PCR. This template volume of 3 μl carried ~100 pg of the cDNA and 10 mM MaCl$_2$ (from the 10× enzyme buffer) which diluted to the optimum of 1.5 mM in the final PCR volume of 20 μl. Since any Mg$^{+2}$ comes from the restriction enzyme buffer, it was not included in the reaction mixture when amplifying secondarily-cut cDNA.

In both cases, i.e., with cutting by a single or by multiple restriction enzymes, bands were extracted from the display gels, reamplified using the 5' and 3' primers, and subcloned into pCRscript with high efficiency using the PCR script cloning kit (Stratagene) and following the manufacturer's instructions. Resulting plasmids were sequenced by cycle sequencing on an Applied Biosystems automated sequencer.

Figure 2:
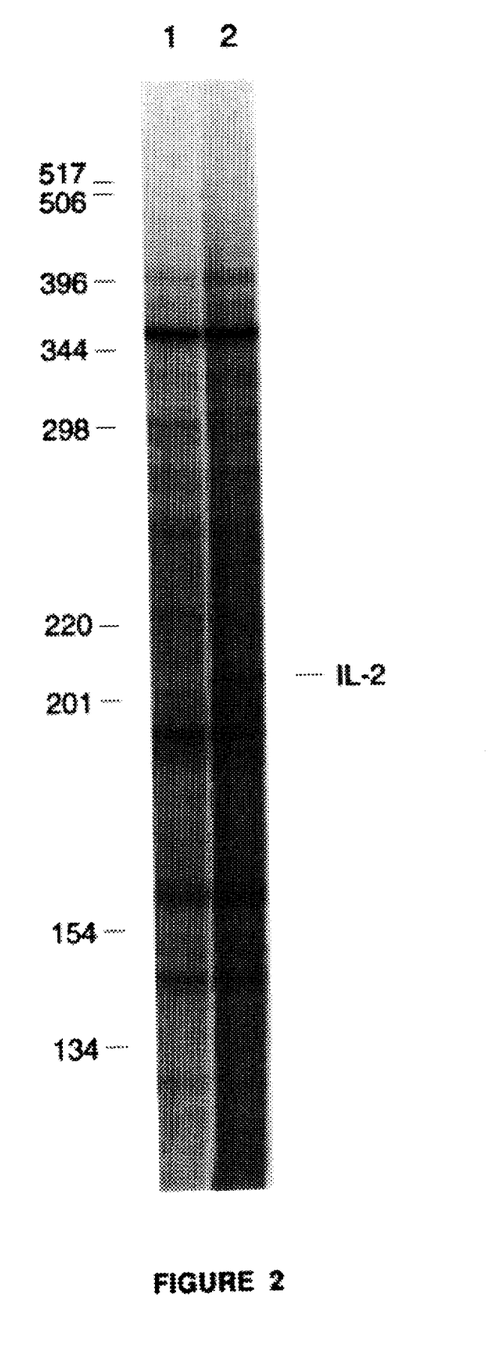
FIG. 2 is a photomicrograph demonstrating the predictability of the band size of known cDNAs on the display gel.

As shown in FIG. 2, the display of BstY1 digested cDNA prepared from resting and activated T-cells produced the predicted 209 nucleotide band corresponding to IL-2 mRNA 3' end sequence in activated T-cells (lane 2), but not in resting T-cells (lane 1). This is because the IL-2 gene will express the corresponding mRNA in the activated, but not in the resting, T-cells.

The total cDNA for the 209 nucleotide sequence is:

| | | | | | |
|---|---|---|---|---|---|
| TAGCGTCCGG | CGCAGCGACG | GCCAGGATCT | TTTATGATTC | TTTTTGTAAG | 50 |
| CCCTAGGGGC | TCTAAAATGG | TTTCACTTAT | TTATCCCAAA | ATATTTATTA | 100 |
| TTATGTTGAA | TGTTAAATAT | AGTATCTATG | TAGATTGGTT | AGTAAAACTA | 150 |
| TTTAATAAAT | TTGATAAATA | TTTTTTTTTT | TTTTTTTTTT | CGCCATTCTA | 200 |
| GGAACTCTC 209 (SEQ. NO. 8) | | | | | |

In this sequence, nucleotides 1 to 25 correspond to A1, nucleotides 26 to 171 correspond to the 146 nucleotide sequence of IL-2 as reported in the literature, nucleotides 172 to 209 correspond to the nucleotides of RP5 beginning with the T18 designation.

After extracting the band from the gel it was confirmed to be IL-2 by sequencing. Before PCR amplification, the adapter ligated cDNA was recut with Alu1, Rsa1 and Msp1 since, without recutting, smeary patterns resulted as BstY1 is a frequently cutting restriction enzyme.

Figure 3:
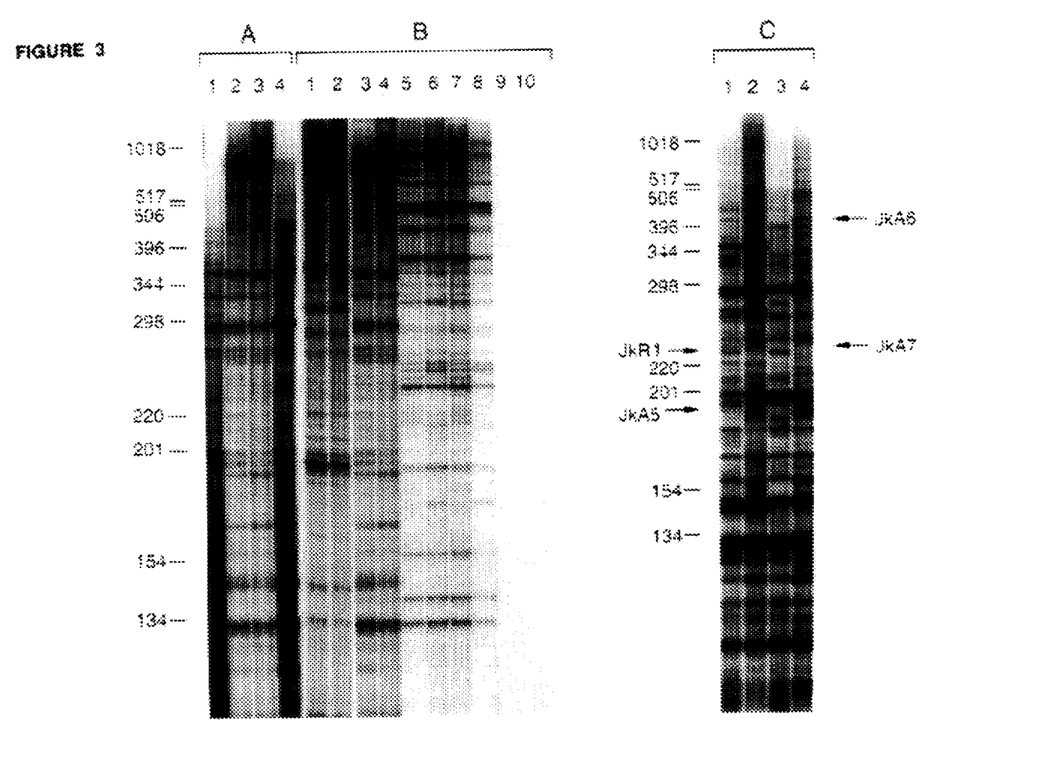
FIG. 3 is a photomicrograph demonstrating the reproducibility patterns and their diversity generated by different restriction enzymes and anchors in oligo-dT primers with heel.

RNA from resting and 4 hour activated Jurkat cells was next compared and displayed in FIG. 3, which shows the reproducibility of display patterns and their diversity generated by different restriction enzymes and anchors in oligo-dT primers with heel.

FIG. 3 depicts three different panels (A, B and C). In panel A, lanes 1 and 2 are the same experiment, run at different times, using resting cells; lanes 3 and 4 are the same experiment, run at different times, using activated cells.

in both panels B and C of FIG. 3, the even numbered lanes are the results of experiments using material from activated T-cells, and the odd numbered lanes are the results of experiments using material from resting T-cells.

In panel B of FIG. 3, lanes 1 and 2 are results from an experiment using a first anchor primer; lanes 3 and 4 are results of the same experiment using a different primer. In lanes 1 to 4, it is readily apparent that by utilizing the same restriction enzyme, but different anchor primers, one will obtain bands of different proteins.

In panel B of FIG. 3, lanes 5 and 6, and 7 and 8, are results of the same experiments and indicate that with the same cDNA but with different restriction enzymes one will obtain different gel patterns.

In panel B of FIG. 3, lanes 9 and 10 are control lanes in which cDNA was cut with restriction enzymes but no adapter or adapter-ligation took place. Thus, lanes 9 and 10 are clear as would be expected of such controls.

As shown in panel C of FIG. 3, sequences that share a common weight but not a common sequence are resolved.

Briefly, this was accomplished by introducing a second restriction enzyme into the reaction mixture after ligation and before amplification by PCR. This will not, statistically, cut strands at the same point in both species of cDNA. Thus, statistically the 3'-end obtained in both species will have different numbers of nucleotides. As described above, when subjected to PCR amplification, only the 3'-end will be amplified (because the 5'-ends will not contain the primer; see FIG. 1, steps 5 and 6). Specifically, in panel C, the material in lanes 1 and 2 was cut utilizing BGIII as the restriction enzyme; the material in lanes 3 and 4 were cut utilizing a second restriction enzyme, HinF1.

The bands seen on the gel for experiments utilizing different restriction enzymes can, as described above, be used to determine the different genes that are up- or down-regulated. For example, the band identified as JkA5 in panel C is present in all lanes indicating that the gene is expressed in all tested preparations of active or resting cells. The band identified as JkA6 is present in lane 4 but not lane 3 indicating that this gene is expressed in activated cells, but is not expressed in resting cells; thus providing a means of determining the state of the cell. The band identified as JkA7 is the same in lanes 1, 2 and 4, but is not present in lane 3; again a means is provided for distinguishing between the state of cells based upon the restriction enzyme used. The band identified as JkA7 is present in lanes 1 and 3, the resting cells, but not in the activated cells which provides a means for determining the status of the cell under examination Therefore, panel A shows that reproducible patterns were observed on display of BgIII digested cDNAs prepared by using oligo-dT primer RP 6.0 from untreated (lanes 1, 2) and activated (lanes 3, 4) Jurkat RNA samples isolated in two separate experiments. Panel B shows lanes 1, 3, 5, 7 and 9 as representing cDNA samples from untreated, and lanes 2, 4, 6, 8 and 10 from activated, Jurkat cells. Although digested with the same restriction enzyme (BgIII), different cDNAs made from one RNA sample using oligo-dT primers with different anchor bases produce different display patterns (RP9.2 in lanes 1 and 2 and RP 6.0 in lanes 3 and 4). When digested with different restriction enzymes (BgIII in lanes 3 and 4 and BamH1 in lanes 5 and 6) cDNA made from one oligo-dT primer RP6.0 produces different display patterns. Reproducible display patterns were observed between lanes 5 and 6 and 7 and 8 when each cDNA sample of untreated (lanes 5, 7) and activated (lanes 6, 8) Jurkat cells were digested with BamH1 in separate tubes and ligated separately before PCR amplification. When aliquots of restriction enzyme digested cDNAs were separately ligated to the adapter at different times identical patterns were observed on PCR amplification. Lanes 9 and 10 represent unligated controls wherein restriction enzyme digested cDNA is utilized for PCR without ligating the adapter. However, bands may appear in these control lanes if there is a contamination of solutions or samples with adapter ligated cDNA. All samples in panels A and B were run on the same gel, however, lanes 1–4 in panel A, 1 and 2 and 3–10 in panel B were run in adjacent lanes on the gel. With regard to panel C, lanes 1 and 3 represent untreated, and lanes 2 and 4 represent activated, Jurkat cDNAs prepared by using oligo-dT primer RP6.0. In lanes 1 and 2, the cDNA was digested with BgIII, while in lanes 3 and 4 BgIII digested and adapter ligated cDNA was redigested with a more frequent cutting restriction enzyme, HinF1, before PCR amplification. Arrows point to the bands that were extracted and found to be true differences. JkA6 and JkA7 in lane 4 were revealed as differences on the display gel only upon recutting the BgI II digested cDNA from lanes 1 and 2 with HinF1 before PCR amplification.

Initially, 3' cDNA fragments produced by restriction enzymes BgIII, BcI1 and BamH1 were displayed in the making of the present invention, and as they produce GATC (SEQ. No. 9) overhangs compatible with the same adapter. These enzymes produced different display patterns with the same pool of cDNAs (see FIG. 3, panel B,). Moreover these patterns were consistently reproducible in several different sets of experimental conditions as described above. The reproducibility of the method was also illustrated by the large number of common bands between untreated and activated Jurkat cDNAs (see FIGS. 2 and 3).

To examine the validity of the method, bands were subcloned, sequenced, and specific pair of oligonucleotide primers based on these sequences were used for RT-PCR [see J. Exp. Med. 174:1259 (1991)] with total RNA from untreated and activated normal T cells and Jurkat cells. Two differences in BgIII digested cDNA (FIG. 3, Panel C, lanes 1 and 2) were verified.

Overlapping bands that mask the true differences can be resolved according to the present invention on recutting the adapter ligated 3'-end cDNA fragments (shown in step 5 of FIG. 1) before PCR amplification. If a site for restriction enzyme used for recutting is present in one of the two comigrating bands it will be cut into one part with the adapter and the other with the heel sequence, neither of which can be amplified by PCR, and will therefore, be eliminated. Using this approach, additional differences between untreated and 4 hour activated Jurkat cells were successfully uncovered when BgI II cut and adapter ligated cDNA were further digested with HinIII (FIG. 3, Panel C, lanes 3 and 4).

Any enzyme or enzymes may be used for primary or secondary cutting and a combination of more than one enzyme can be used for recutting. Another advantage of recutting is that recovery of low abundance cDNAs is enhanced because removal of high abundance bands by recutting allows access of these fragments to PCR primers (FIG. 3, panel C, lanes 3 and 4). In addition, recutting can be used to minimize redundancy between fragments in different lanes. For example, BgIII cut cDNA fragments can be recut with BamHI and vice versa, so that the two samples share no amplified products. A large number of variations of the display patterns can, therefore, be produced by the method according to the present invention to look for differentially expressed genes by (i) a combination of a number of different two base anchored, heeled oligo dT for making cDNAs, (ii) a number of different restriction enzymes that can be used for primary cutting of these cDNAs and, (iii) the number of restriction enzymes used for secondary cutting for each primary cut.

Figure 4:
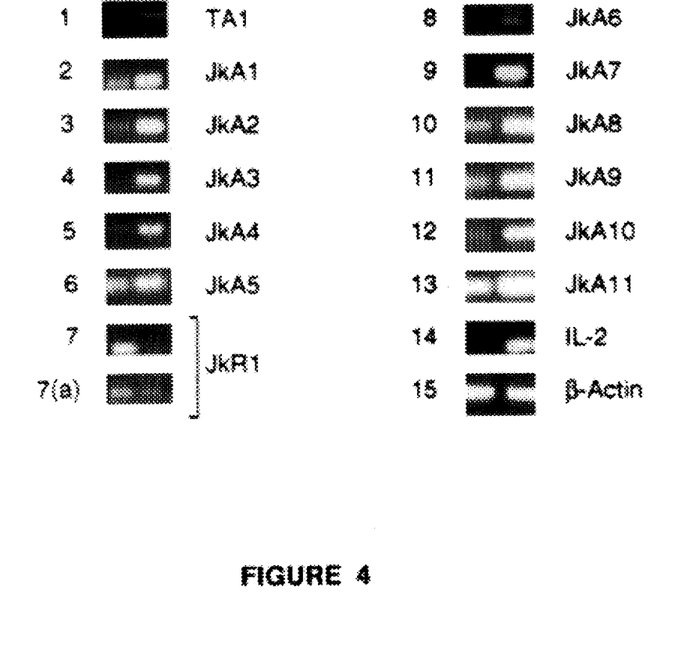
FIG. 4 is a photomicrograph demonstrating a verification of differences from display gel by RT-PCR of original total RNA sample.

Consistent with the reproducibility of the gel patterns, most differences in the intensity of cDNA amplification products corresponded to differences in mRNA levels. For example, a total of 15 bands were subcloned, sequenced and examined by RT-PCR of these bands, fourteen showed changes in levels of expression predicted from the gel pattern (FIG. 4, in which the left lane represents material from resting cells, and the right lane represents material from active cells, in addition, sequence 7 represents a band from a normal T-cell, and sequence 7A represents a band from a cancerous T-cell). Of the fourteen sequences, one was myc, one IL-2 and the remainder were novel sequences not represented in conventional sequence databases. Each product contained a polyadenylation signal upstream of the oligo-dT tract. At the other end of each product, the expected four base overhang of the adapter was seen, followed by the base predicted from the specificity of the enzyme used for the initial cutting of the cDNA. For example, bands from display patterns generated with the enzyme BgI II all had the sequence of the adapter including the GATC (SEQ. NO. 9) of the adapter overhang, followed by a T that would be expected if the 5' end of the attached cDNA had been generated by BgI II. In every instance, bands recovered from the gel lacked internal cleavage sites for the restriction enzymes used for primary or secondary cutting. The levels of PCR products of the twelve induced and one down-regulated cDNAs, and presumably their mRNAs, vary with respect to the levels IL-2 and β-Actin (FIG. 4). Therefore, while it is easier to detect and isolate cDNA fragments corresponding to the more abundant mRNAs, the approach according to the present invention provides the ability to detect and subclone samples from quite rare mRNAs.

More specifically with regard to FIG. 4, verification of differences from display gel by RT-PCR of original total RNA sample is shown. In each of the panels 1–15, the left lane represents untreated while the right lane represent activated Jurkat cDNA (In panel 7, however, peripheral blood T-cell RNA was used for RT-PCR). Bands of interest were extracted from the display gel, subcloned, sequenced, and specific PCR primers were made. The method to prepare RNA and RT-PCR has been described [see J. Exp. Med. 174:1259 (1991)]. Briefly, 1 µg of total RNA was reverse transcribed using 100 ng of random hexamer primer in a total volume of 20 µl. Following heat inactivation of reverse transcriptase, the final volume of the reaction mix was adjusted to 50 µl with water, 2 µl of this diluted sample was taken in the final PCR reaction mixture containing 5 µl of 10× PCR buffer (100 mM Tris.HCl and 500 mM KCl), 200 nM of each of the 5' and 3' primers, 200 µM dNTPs, 1 unit of Amplitaq and 1.5 mM MgCl$_2$. PCR consisted of 30 cycles of 94° C. for 30 seconds 55° C. for 1 minute and 72° C. for 30 seconds. PCR samples were analyzed on 1.5% agarose gel and stained with ethidium bromide. Samples in panels 1–15 were analyzed separately, however, IL-2 and β-Actin always showed the same patterns in each experiment as in panels 14 and 15 respectively.

One of the most important factors affecting clarity of the display patterns is the quantity of template for PCR and the number of PCR cycles. We found ~100 pg of cDNA template is appropriate for PCR amplification. However, before attempting to analyze differences in display gels, we routinely PCR amplified serial dilutions of the template to choose a concentration that would produce clear and reproducible patterns in 28–30 PCR cycles. High template concentrations produced smeary patterns while at very low template concentration, bands started to drop out, producing artefactual differences on the gel. Good quality of RNA is also a prerequisite for clean display patterns. Replicates of PCR amplified samples were run on the gel to look for the consistency in the difference of intensity of the band under consideration and unligated cDNAs were PCR amplified as controls that showed bands only if there was contamination of adapter ligated cDNA in solutions or sample. We found subcloning a band of interest better than direct analysis of the reamplified band recovered from the gel and it is necessary to examine that recovered band is of the correct size.

Increasing the number of 3' cDNA end fragments in a sample can cause blurred patterns. Sau3A1 (a four base cutter) produced smeary patterns although the same amount of cDNA digested with BgIII or BamH1 (six base cutters) produced clear gel patterns. Sau3A1 is a frequent cutter and produces more amplifiable 3'-ends from a cDNA population which then crowd together on the gel. RNA primed with oligo-dT primers containing a mixture of bases in the subterminal anchor position produced crowded patterns because a larger number of cDNA molecules were synthesized.

The extent to which anchored oligo-dT primers prime cDNA synthesis from mRNAs whose sequence does not match the anchor bases perfectly has been a major limitation of cDNA display methods. In the present invention a number of conditions to enhance specificity of this priming were examined, and it was found that primer extension by reverse transcriptase at 50° C. was optimal. However, even under these optimized conditions some known cDNA products arose because of mispairing or looping out of the subterminal anchor base. Nevertheless, different yet consistent and reproducible patterns were obtained with cDNAs made from oligo-dT primers with different anchor bases.

Overall, from four pairs of lanes representing untreated and activated Jurkat cell mRNAs, about 700 bands could be evaluated. Of these, about 4% appeared to represent species that increase (up-regulated) on activation and as many as 2% significantly decreased (down-regulated) on activation. T-cell activation is an extensively studied phenomenon and about 80 genes whose expression is increased in the early phase of activation have been recognized [see Annul. Rev. Immunol. 8:421 (1990)]. In the present experiments, the estimated number of 3'-end mRNA sequences whose expression is altered within four hours after T-cell activation is an order of magnitude higher than might be presumed from earlier studies [see Proc. Natl. Acad. Sci. 84:1609 (1987); Nature 308:149 (1984); and Mol. Cell Biol. 9:1041 (1989)]. However, one limitation common to all methods of 3'-end cDNA display is that apparent differences in expression may arise if sites of polyadenylation of a single species of mRNA changed after activation.

One cDNA, JkR1, that was down-regulated on activation in both peripheral blood T-cells and Jurkat cells was chosen for further study. Down-regulation of JkR1 in peripheral blood T-cells was evident 4 hours after activation with the addition of ionomycin and diacylglycerol. When resting T-cells were exposed to actinomycin D, JkR1 mRNA was relatively stable for up to 3 hours. This raises the possibility that part of the down-regulation might be activated by mRNA destabilization. Phillipson has studied a small group of GAS genes whose mRNA declines on refeeding cells with serum [see Cell 54:787 (1988)], and several of these mRNAs were also down-regulated by destabilization [see Mol. Cell Biol. 6:2924 (1990)]. However, JKR1 is different from the GAS genes both in sequence and in the fact that the level of its mRNA was not depressed simply by refeeding but only after specific activation of T-cells.

Strikingly, there are very few references in the literature to genes whose expression is down regulated on T-cell activation [see Nucleic Acids Res. 19:4655 (1991); and Proc. Natl. Acad. Sci. USA 90:10260 (1993)]. This suggests that changes in the intracellular environment upon T-cell activation is a combined result of down-regulation of a set of genes in addition to induction of gene expression.

The method of the present invention has shown the ability to uncover multiple differences between rather similar samples of untreated and 4 hr activated Jurkat T-Cells. The reproducibility and extensive representation obtained with this method allows a systematic analysis of a sample, taking full advantage of sequence databases. Since the lane and size of the band of a known gene can be easily predicted, gel patterns can be used to evaluate changes in the level of expression of known mRNAs without resorting to cloning or further analysis. As a large fraction of cDNAs become represented in the databases as 3' ESTs, one can use data base searches to limit or define candidate genes corresponding to any band whose abundance changes. This will be an increasingly powerful approach as more cDNA and genomic sequences accumulate. Furthermore, by using fluorescent primers, automated analysis of the control and test samples can be carried out in a single lane. And finally, the use of two different restriction sites, one for the adapter and the other for the heel primer can expedite and orient the cloning. Because of its sensitivity, this approach could be used to study the time course of appearance or disappearance of a set of mRNAs in a variety of eukaryotic systems and extrapolate back to shorter time intervals after the initiating stimulus is applied.

In summary, the present invention provides an approach to study changes in gene expression by selective PCR amplification and display of 3'-end restriction fragments of double stranded cDNAs. The method according to the present invention produces highly consistent and reproducible patterns, can detect almost all mRNAs in a sample, and can resolve hidden differences such as bands that differ in their sequence but comigrate on the gel. Bands corresponding to known cDNAs move to predictable positions on the gel, making this a powerful approach to correlate gel patterns with cDNA databases. Applying the method according to the present invention, we have examined differences in gene expression patterns during T-cell activation. Of a total of 700 bands that were evaluated during the making of the present invention, as many as 3-4% represented mRNAs that are up-regulated, while about 2% were down-regulated within 4 hours of activation of Jurkat T-cells. These results suggest that the method according to the present invention is suitable for the systemic, expeditious and nearly exhaustive elucidation of subtle changes in the patterns of gene expression in cells which altered physiologic states.

Thus while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. For example, while the gels prepared and shown in the figures are prepared according to conventional gel technology, the fragments run in these gels may be alternatively labelled with fluorescent labels and the reading of the gels conducted by automated means. Also, while specific sized oligonucleotide primers are depicted in the embodiments described herein, the exact length and nucleotide sequence of these primers may be varied while still maintaining the requirements that these primers must have as described herein. Also, while the embodiment described herein is directed primarily at the assay of changes occurring in activated and resting cells, it is to be understood that whenever a cell is brought into contact with an exogenous material such as for example a pharmaceutical or toxic compound, the cell will invariably provide some genetic response to the material resulting in the up- or down-regulation of genetic expression; these changes can also be noted using the method according to the present invention with very little alteration to the general scheme of the method depicted in FIG. 1, and these changes can be used to evaluate the effect that such materials have on the host cell that has been exposed to the material. Accordingly, such changes, modifications, alterations and uses are properly intended to be within the full range of equivalents, and therefore within the purview of the following claims.

Having thus described our invention and the manner and process of making and using it in such full, clear, concise, and exact terms so as to enable any person skilled in the art to which it pertains, or with it is most nearly connected, to make and use the same.

We claim:

1. A method for selectively amplifying in a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridzes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other; and (f) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, thereby selectively amplifying a DNA fragment comprising sequence complementary to a 3' end of an mRNA.

2. The method of claim 1, wherein the 5' sequence of the oligonucleotide primer of step (a) comprises a sequence that provides a restriction enzyme site in the duplex of step (c).

3. The method of claim 1, wherein the adapter comprises a first portion, wherein the two strands are noncomplementary to each other and a second portion, wherein the two strands are complementary to each other, resulting in a partially hybridized adapter that is Y-shaped.

4. The method of claim 1, wherein one of the two strands of the non-complementary portion comprises a sequence that provides a restriction enzyme site in the amplified fragment of step (f).

5. The method of claim 1, wherein the mRNA is isolated from cells or tissue.

6. The method of claim 1, wherein at least one of the primers in step (f) is labeled.

7. The method of claim 6, wherein the label is a fluorescent label.

8. A method for selectively isolating in a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridizes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, to produce an amplified fragment comprising sequence complementary to a 3' end of an mRNA; and (g) isolating the amplified fragment.

9. A method for selectively cloning from a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridizes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other; and (f) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, to produce an amplified fragment comprising sequence complementary to a 3' end of an mRNA;

(g) isolating the amplified fragment; and (h) cloning the isolated fragment.

10. A method for analyzing in a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridizes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, to produce an amplified fragment comprising sequence complementary to a 3' end of an mRNA;

(g) isolating the amplified fragment;

(h) cloning the isolated fragment; and (i) analyzing the cloned fragment by DNA sequence analysis.

11. A method for selectively detecting in a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridizes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, to produce an amplified fragment comprising sequence complementary to a 3' end of an mRNA; and (g) detecting the amplified fragment.

12. A method for selectively amplifying in a nucleic acid sample a DNA fragment having sequence complementary to a 3' end of an mRNA, comprising the steps of:

(a) contacting the mRNA with an oligonucleotide primer comprising a 5' sequence incapable of hybridizing to a polyA tail of the mRNA, and a 3' sequence that hybridizes to a portion of the polyA tail of the mRNA and at least one non-polyA nucleotide immediately upstream of the polyA tail;

(b) reverse transcribing the mRNA to produce a first strand cDNA that includes the oligonucleotide primer;

(c) synthesizing a second DNA strand complementary to the first strand cDNA to form a duplex;

(d) cleaving the duplex with at least one sequence-specific cleaving agent to provide a number of duplex cleavage fragments;

(e) ligating an adapter to the cleavage fragments, the adapter consisting of two partially hybridized nucleic acid strands, wherein portions of the two strands are non-complementary to each other and portions of the two strands are complementary to each other;

(f) reacting at least one sequence-specific cleaving agent with the ligated fragments; and (g) amplifying the ligated cleavage fragments using a first primer whose sequence comprises at least a portion of the 5' sequence of the oligonucleotide primer of step (a) and a second primer whose sequence comprises at least a portion of the sequence of one strand of the adaptor in the non-complementary portion, thereby selectively amplifying a DNA fragment comprising sequence complementary to a 3' end of an mRNA.

13. A method for comparing the levels of mRNA expression in two cell populations, comprising:

selectively amplifying in a nucleic acid sample from each cell population a DNA fragment comprising sequence complementary to a 3' end of an mRNA according to the method of claim 5; and comparing the amounts of amplified fragments obtained in step (f) of claim 5.

14. The method of claim 13, wherein at least one of the primers for amplification is labeled.

15. The method of claim 14, wherein the label is a radiolabel or fluorescent label.

16. The method of claim 13, wherein one of the cell populations is treated.

* * * * *

UNITED STATES PATENT AND TRADEMARK OFFICE
CERTIFICATE OF CORRECTION

PATENT NO. : 5,712,126
DATED : January 27, 1998
INVENTOR(S) : Weissman and Prashar It is certified that error appears in the above-identified patent and that said Letters Patent is hereby corrected as shown below:

In column 19, claim 12, line 37, after "a" delete "nuclcic" and substitute therefor -- nucleic --.

In column 20, claim 13, line 32, after "claim" delete "5;" and substitute therefor -- 1; --

In column 20, claim 13, line 34, after "claim" delete "5." and substitute therefor --1. --.

Signed and Sealed this

First Day of September, 1998

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 6 base pairs
( B ) TYPE:nucleic acid
( C ) STRANDEDNESS:single
( D ) TOPOLOGY:linear ( i i ) MOLECULE TYPE:DNA ( x i ) SEQUENCE DESCRIPTION: SEQ ID NO:1:

AATAAA  6

( 2 ) INFORMATION FOR SEQ ID NO:2:

( i ) SEQUENCE CHARACTERISTICS:
( A ) LENGTH: 40 base pairs
( B ) TYPE:nucleic acid
( C ) STRANDEDNESS:single
( D ) TOPOLOGY:linear ( i i ) MOLECULE TYPE:DNA ( x i ) SEQUENCE DESCRIPTION: SEQ ID NO:2:

CTCTCAAGGA TCTTACCGCT TTTTTTTTT TTTTTTTAT  40

( 2 ) INFORMATION FOR SEQ ID NO:3:

( i ) SEQUENCE CHARACTERISTICS:

( A ) LENGTH: 40 base pairs
            ( B ) TYPE:nucleic acid
            ( C ) STRANDEDNESS:single
            ( D ) TOPOLOGY:linear ( i i ) MOLECULE TYPE:DNA ( x i ) SEQUENCE DESCRIPTION: SEQ ID NO:3:

TAATACCGCG CCACATAGCA TTTTTTTTTT TTTTTTTCG          40

( 2 ) INFORMATION FOR SEQ ID NO:4:

( i ) SEQUENCE CHARACTERISTICS:
            ( A ) LENGTH: 40 base pairs
            ( B ) TYPE:nucleic acid
            ( C ) STRANDEDNESS:single
            ( D ) TOPOLOGY:linear ( i i ) MOLECULE TYPE:DNA ( x i ) SEQUENCE DESCRIPTION: SEQ ID NO:4:

CAGGGTAGAC GACGCTACGC TTTTTTTTT TTTTTTTGA          40

( 2 ) INFORMATION FOR SEQ ID NO:5:

( i ) SEQUENCE CHARACTERISTICS:
            ( A ) LENGTH: 25 base pairs
            ( B ) TYPE:nucleic acid
            ( C ) STRANDEDNESS:single
            ( D ) TOPOLOGY:linear ( i i ) MOLECULE TYPE:DNA ( x i ) SEQUENCE DESCRIPTION: SEQ ID NO:5:

TAGCGTCCGG CGCAGCGACG GCCAG          25

( 2 ) INFORMATION FOR SEQ ID NO:6:

( i ) SEQUENCE CHARACTERISTICS:
            ( A ) LENGTH: 29 base pairs
            ( B ) TYPE:nucleic acid
            ( C ) STRANDEDNESS:single
            ( D ) TOPOLOGY:linear ( i i ) MOLECULE TYPE:DNA ( x i ) SEQUENCE DESCRIPTION: SEQ ID NO:6:

GATCCTGGCC GTCGGCTGTC TGTCGGCGC          29

( 2 ) INFORMATION FOR SEQ ID NO:7:

( i ) SEQUENCE CHARACTERISTICS:
            ( A ) LENGTH: 19 base pairs
            ( B ) TYPE:nucleic acid
            ( C ) STRANDEDNESS:single
            ( D ) TOPOLOGY:linear ( i i ) MOLECULE TYPE:DNA ( x i ) SEQUENCE DESCRIPTION: SEQ ID NO:7:

TAGCGTCCGG CGCAGCGAC          19

( 2 ) INFORMATION FOR SEQ ID NO:8:

( i ) SEQUENCE CHARACTERISTICS:
            ( A ) LENGTH: 209 base pairs
            ( B ) TYPE:nucleic acid
            ( C ) STRANDEDNESS:single
            ( D ) TOPOLOGY:linear (i i) MOLECULE TYPE:DNA (x i) SEQUENCE DESCRIPTION: SEQ ID NO:8:

```
TAGCGTCCGG CGCAGCGACG GCCAGGATCT TTTATGATTC TTTTTGTAAG    50
CCCTAGGGGC TCTAAAATGG TTTCACTTAT TTATCCCAAA ATATTTATTA   100
TTATGTTGAA TGTTAAATAT AGTATCTATG TAGATTGGTT AGTAAAACTA  150
TTTAATAAAT TTGATAAATA TTTTTTTTTT TTTTTTTTTT CGCCATTCTA  200
GGAACTCTC                                                209
```

(2) INFORMATION FOR SEQ ID NO:9:

(i) SEQUENCE CHARACTERISTICS:
        (A) LENGTH: 4 base pairs
        (B) TYPE:nucleic acid
        (C) STRANDEDNESS:single
        (D) TOPOLOGY:linear     (i i) MOLECULE TYPE:DNA     (x i) SEQUENCE DESCRIPTION: SEQ ID NO:9:

```
GATC    4
```

(2) INFORMATION FOR SEQ ID NO:10:

(i) SEQUENCE CHARACTERISTICS:
        (A) LENGTH: 20 base pairs
        (B) TYPE:nucleic acid
        (C) STRANDEDNESS:single
        (D) TOPOLOGY:linear     (i i) MOLECULE TYPE:DNA     (x i) SEQUENCE DESCRIPTION: SEQ ID NO:10:

```
CTCTCAAGGA TCTTACCGCT    20
```

(2) INFORMATION FOR SEQ ID NO:11:

(i) SEQUENCE CHARACTERISTICS:
        (A) LENGTH: 20 base pairs
        (B) TYPE:nucleic acid
        (C) STRANDEDNESS:single
        (D) TOPOLOGY:linear     (i i) MOLECULE TYPE:DNA     (x i) SEQUENCE DESCRIPTION: SEQ ID NO:11:

```
TAATACCGCG CCACATAGCA    20
```

(2) INFORMATION FOR SEQ ID NO:12:

(i) SEQUENCE CHARACTERISTICS:
        (A) LENGTH: 20 base pairs
        (B) TYPE:nucleic acid
        (C) STRANDEDNESS:single
        (D) TOPOLOGY:linear     (i i) MOLECULE TYPE:DNA     (x i) SEQUENCE DESCRIPTION: SEQ ID NO:12:

```
CAGGGTAGAC GACGCTACGC    20
```